US00PP09207P

United States Patent [19]

van Diemen

[11] Patent Number: Plant 9,207

[45] Date of Patent: Jul. 18, 1995

[54] *FICUS BENJAMINA* PLANT NAMED 'WIANDI'

[75] Inventor: Hubertus T. van Diemen, Aalsmeer, Netherlands

[73] Assignee: Kwekerij De Amstel, B.V., Aalsmeer, Netherlands

[21] Appl. No.: 250,273

[22] Filed: May 27, 1994

[51] Int. Cl.[6] ..... A01H 5/00

[52] U.S. Cl. ..... Plt./88.9

[58] Field of Search ..... Plt. 88.9

[56] References Cited

U.S. PATENT DOCUMENTS

P.P. 8,929 10/1994 van Diemen ..... Plt./88.9

OTHER PUBLICATIONS

Dialog Printout. File 658: Trademark Scan (R): Benelux, 1994 Compu-Mark N.V. "Wiandi".

*Primary Examiner*—Howard J. Locker

*Attorney, Agent, or Firm*—Christie, Parker & Hale

[57] ABSTRACT

A *Ficus benjamina* plant having an irregular growth habit and horizontally zig-zag branching pattern.

1 Drawing Sheet

BACKGROUND OF THE INVENTION

The present invention comprises a new and distinct cultivar of *Ficus benjamina.* The varietal denomination of the new cultivar is 'Wiandi'.

The new variety was discovered as a mutation in a controlled planting of *Ficus benjamina* 'Natasha' in a greenhouse in Aalsmeer, The Netherlands. The new cultivar was discovered as a whole plant mutation and was isolated in a glass house in Aalsmeer, Holland.

SUMMARY OF THE INVENTION

The new variety is a mutation of the variety *Ficus benjamina* 'Natasha' and differs significantly in growth habit and appearance from its parent. Whereas *Ficus benjamina* 'Natasha' exhbits a vertical, upright growth pattern which reaches a height of one meter in approximately nine months, 'Wiandi' will take approximately two years to reach this height. Also, the growth pattern of 'Wiandi' is irregular and the growth form is substantially horizontal, or laterally dominant with zig-zag pattern between internodal spacing. Although growth of the new variety will eventually progress vertically, it does so much slower than its parent, as indicated above.

The new variety has been asexually reproduced vegetatively by rooted cuttings in Aalsmeer, The Netherlands. Asexual reproduction through succeeding generations has established that the combination of characteristics as herein disclosed for the new cultivar is firmly fixed and is retained through successive generations of asexual reproduction.

The term "Zig-Zag" is an acceptable botanical term denoting a botanical growth form. As used herein, the new variety, 'Wiandi,' maintains a decumbant growth pattern in addition to its irregular branching. Its growth habit is horizontally dominant as opposed to apically dominant Ficus varieties like the parent 'Natasha', and *Ficus benjamina.* Its branches take irregular angular turns between leaf internodes and internode distance is also irregular. Lengths between leaf internodes on the same branch have been measured at 7 mm, 11 mm, 18 mm and 20 mm. These length differences do not appear to fall into any pattern along the branch, but are observed at random. For instance, internode length does not necessarily increase or decrease laterally along a branch. In addition, it is very rare to find a successive internode that does not angle off from its preceding internode. Growth does not continue along a relatively straight line as it does with 'Natasha'. Without manipulation or pruning, it is not uncommon to see angulation of successive internodes as great as 90°. Greater angulation of branching has been achieved or induced by pruning of the apical branch tip. With pruning, angulation of the growth between internodes has been observed as great as 150°. 'Wiandi' also has been observed to throw multiple ariel roots (branch prop type), particularly when grown under hot humid contitions such as in Homestead, Fla., during the months of January to September. In Florida, it has been observed that the leaf size increases during the warmer months, as does Ficus 'Natasha', and then decreases during the cooler months. Leaf sizes stated previously indicate the smaller leaf size cycle which is most typical of the plant.

BRIEF DESCRIPTION OF THE ILLUSTRATION

The accompanying illustration shows a specimen of the new cultivar in a photo illustration as true to color as is reasonably possible to make in an illustration of this character, and illustrates the zig-zag branching growth habit.

DESCRIPTION OF THE NEW VARIETY

'Wiandi' has not been observed under all possible environmental conditions. The phenotypic expression may vary with variations in environment such as temperature, light intensity and day length. The following observations and descriptions are of plants grown in Aalsmeer, the Netherlands, in a greenhouse. In this description, color references are to The Royal Horticultural Society Colour Chart (RHSCC). The terminology used in the color descriptions herein refers to plate numbers in this color chart.

Classification:

*Botanical.—Ficus benjamina* cv. 'Wiandi'.

Parentage: Mutation of *Ficus benjamina* Natasha.

Propagation: By vegetative cuttings and other known asexual reproduction techniques, such as tissue culture.

PLANT

A. Form: Multiple laterally zig-zag branching woody ornamental.

B. Growth: Vigorous, multiple irregular zig-zag branching.

*Height attained.*—About one meter after two years.

C. Foliage:

1. *Size.*—About 2 cm wide by about 4 to 5 cm long (to leaf tip). Small, elliptical, ovate and tend to curl downward at the acuminate tip.
2. *Quantity.*—Multiple, numerous, in relation to other *Ficus benjamina* cultivars. Subject to the prior discussion about internode spacing for 'Wiandi', it may be noted that average internode spacing of a *Ficus benjamina* is about 47 mm, which may increase with light reduction, whereas the average internode spacing of 'Wiandi' is 14 mm. Therefore, the foliage or number of leaves per running meter of branch of 'Wiandi' is greater than that of other *Ficus benjamina* varieties.
3. *Color.*—New Foliage: Upper side — near 144A; juvenile leaves light green and glossy, near 144A on both top and underside of juvenile leaves. Old Foliage: Upper side — near 147A, darker green, leathery appearance, underside of mature leaves is near 137C.
4. *Shape.*—Ovate elliptical — acuminate leaf tip, curling downward.
5. *Texture.*—Smooth, glossy turning leathery.
6. *Veination.*—Insignificant, 1 mm or less, each leaf is costate or bisected by one prominent vein running from petiole to leaf tip. All other veination is so minute as to be insignificant. The single vein is observed more prominently from the underside of the leaf, is convex, and is a light yellow-green color, near 145A.
7. *Edge.*—Smooth.
8. *Petiole.*—Near 199A; about 10 mm long, light green.
9. *Resistance to disease.*—Resistant to anthracnose, *Agrobacterium radiobacter, Agrobacterium tumefaciens, Heterodera fici.*

D. Wood:

*New shoots.*—Color — near 191B; the juvenile wood is a darker grayish brown than the more mature wood, near 199B.

Note: To date, and under conditions described herein the new variety has not borne flowers or fruit.

Temperature range: To 0° C., will resist to −1° C., some frost damage will occur when 'Wiandi' is exposed to 0° C. and at −1° C. sustained for 2 hours, total dieback can be expected.

Internode spacing: Variable, irregular, betwen about 9–11 cm.

Preferred growing conditions: 20° C. to 32° C.

Growth habit: Multiple laterally zig-zag branching, woody ornamental. The growth as stated previously, is multiple branching with alternating petioles and leaves, internode spacing is irregular and angular branching is unpredictable.

Leaves per stem: Multiple, alternative, irregular.

Reproductive organs: Not available.

I claim:

1. A new and distinct cultivar of *Ficus benjamina* substantially as illustrated and described.

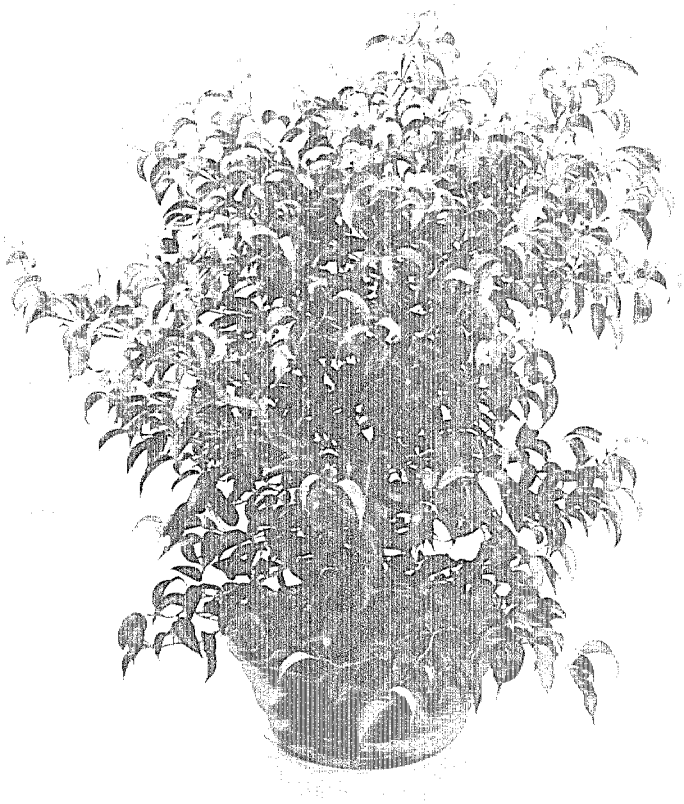

* * * * *